(12) United States Patent
Canady

(10) Patent No.: US 7,578,817 B2
(45) Date of Patent: Aug. 25, 2009

(54) COMBINATION ARGON PLASMA COAGULATION AND ELECTROCAUTERY DEVICE AND METHOD

(76) Inventor: Jerome Canady, 1119 Jefferson St., McKeesport, PA (US) 15132

( * ) Notice: Subject to any disclaimer, the term of this patent is extended or adjusted under 35 U.S.C. 154(b) by 474 days.

(21) Appl. No.: 11/199,631

(22) Filed: Aug. 9, 2005

(65) Prior Publication Data

US 2006/0036239 A1 Feb. 16, 2006

Related U.S. Application Data

(60) Provisional application No. 60/600,550, filed on Aug. 11, 2004.

(51) Int. Cl.
*A61B 18/14* (2006.01)
(52) U.S. Cl. .......................... 606/45; 606/49
(58) Field of Classification Search ............ 606/49, 606/45
See application file for complete search history.

(56) References Cited

U.S. PATENT DOCUMENTS

| | | |
|---|---|---|
| 4,040,426 A | 8/1977 | Morrison |
| 4,781,175 A | 11/1988 | McGreevy |
| 5,108,392 A | 4/1992 | Spingler |
| 5,122,138 A | 6/1992 | Manwaring |
| 5,207,675 A | 5/1993 | Canady |
| 5,217,460 A | 6/1993 | Knoepfler |
| 5,330,469 A | 7/1994 | Fleenor |
| 5,464,405 A | 11/1995 | Fujitsu |
| 5,542,945 A | 8/1996 | Fritzsch |
| 5,556,397 A | 9/1996 | Long et al. |
| 5,603,712 A | 2/1997 | Koranda et al. |
| 5,658,281 A | 8/1997 | Heard |
| 5,720,745 A | 2/1998 | Farin et al. |
| 5,746,739 A | 5/1998 | Sutter |
| 6,149,620 A | 11/2000 | Baker et al. |
| 6,197,026 B1 | 3/2001 | Farin et al. |
| 6,231,574 B1 | 5/2001 | Posthuma |
| 6,283,963 B1 | 9/2001 | Regula |
| 6,293,946 B1 | 9/2001 | Thorne |
| 6,458,124 B1 | 10/2002 | Garito |
| 6,458,125 B1 | 10/2002 | Cosmescu |
| 6,464,701 B1 | 10/2002 | Hooven et al. |
| 6,558,379 B1 | 5/2003 | Batchelor et al. |
| 6,585,735 B1 | 7/2003 | Lands et al. |
| 2002/0095152 A1 | 7/2002 | Ciarrocca |

*Primary Examiner*—Lee S Cohen
(74) *Attorney, Agent, or Firm*—24IP Law Group; Timothy R. DeWitt

(57) ABSTRACT

A combination argon plasma coagulation (APC) and monopolar electrosurgical device and method are shown. An electrosurgical tool such as a spatula, hook, ball, or the like has a neck and a plurality of members biased to an open position. The electrosurgical tool is connected to the shaft having a channel therein for accommodating an APC probe. A collet is placed on the shaft and is provided with a mechanism such as threads to permit movement of the collet with respect to the shaft. Such movement causes the plurality of members of the surgical tool to move being open and closed positions.

7 Claims, 1 Drawing Sheet

COMBINATION ARGON PLASMA COAGULATION AND ELECTROCAUTERY DEVICE AND METHOD

CROSS-REFERENCE TO RELATED APPLICATIONS

Figure 1:
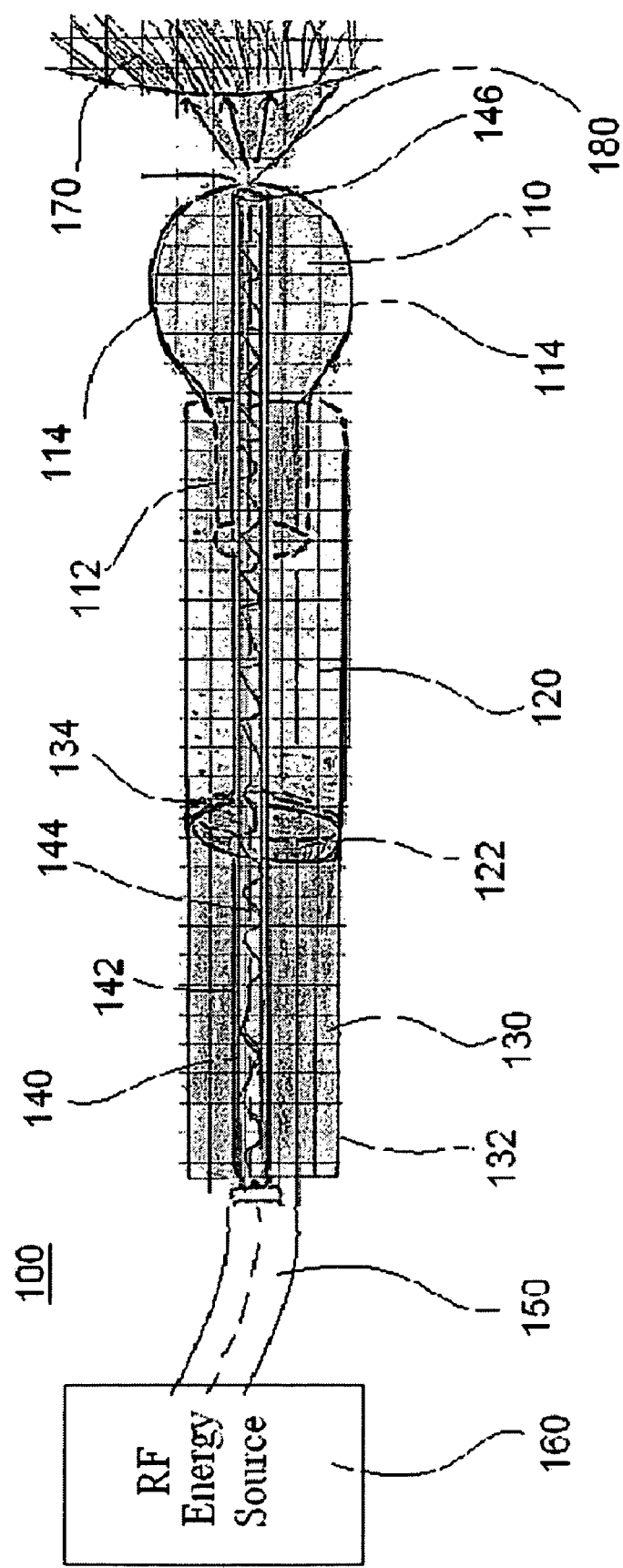

This application claims the benefit of the filing date of U.S. Provisional Application Ser. No. 60/600,550 entitled "Combination Argon Plasma Coagulation and Electrocautery Device and Method," and filed on Aug. 11, 2004 by inventor Jerome Canady.

The above cross-referenced related application is hereby incorporated by reference herein in its entirety.

STATEMENT REGARDING FEDERALLY SPONSORED RESEARCH OR DEVELOPMENT

Not applicable.

BACKGROUND OF THE INVENTION

1. Field of the Invention

The present invention relates to surgical device capable of performing both argon plasma coagulation and electrocautery in open and minimally invasive surgery.

2. Brief Description of the Related Art

Controlling or arresting blood loss is of high priority during surgery so as to avoid or minimize the necessity of introducing foreign blood or blood products into a patient. This has increased in importance due to concern over contamination of the blood supply by viral agents which cause, for example, acquired immune deficiency syndrome (AIDS), hepatitis, and the like.

Standard means for controlling traumatic and surgical blood loss are electrosurgical generators and lasers, which respectively direct high-frequency electrical currents or light energy to localize heat in bleeding vessels so as to coagulate the overlying blood and vessel walls.

Argon beam coagulators additionally have been demonstrated to be effective tissue coagulators. Examples of argon beam coagulators for use in open surgery can be found in U.S. Pat. No. 4,040,426 to Morrison and U.S. Pat. No. 4,781,175 to McGreevy. Argon beam coagulators for use rigid and flexible endoscopy also are known. An example of a device for flexible endoscopy may be seen in U.S. Pat. No. 5,207,675 to the present inventor. In some embodiments in that patent, the inventor disclosed dual modality devices that could be used either for argon plasma coagulation or for traditionally electrocautery in an endoscopic environment. The inventor also disclosed an embodiment having the dual modality of argon plasma coagulation and endoscopic biopsy forceps. In that embodiment, argon plasma coagulation could be used by a surgeon while the biopsy forceps were withdrawn inside the flexible endoscopic tube. The biopsy forceps could then be extended and used, but argon plasma coagulation was not performed with the biopsy forceps extended from the end of the tube.

Various electrodes for use in monopolar electrosurgery have been known for many years. Examples of such various electrodes are spatula electrodes, spoon electrodes, ball tip electrodes, hook electrodes and flat blade electrodes. Such electrodes have functioned well and been useful, but they, along with many of the argon plasma coagulation devices referenced above, have suffered from the drawback of surgeons not be able to rapidly switch from performing electrocautery to argon plasma coagulation and back again.

An exception to that limitation is disclosed in U.S. Pat. No. 5,207,675, discussed above, which discloses dual modality devices for endoscopic surgery. Those device include structure for retracting an electrocautery wire or tool such as forceps inside a flexible tube so that argon plasma coagulation may be performed. To revert to traditional electrosurgery, the surgeon can extend the wire or tool outside the tube for touching the tissue. While the devices of this patent function well and are very useful, particularly for electrocautery wires, forceps, snares, needles and biopsy tools that are small enough to fit within the small flexible tube, a need exists for dual mode devices that can accommodate somewhat larger electrosurgical tools such as spatulas, balls, hooks and the like.

SUMMARY OF THE INVENTION

A combination argon plasma coagulation and monopolar electrosurgery device and method are disclosed. A preferred embodiment of the invention has an argon plasma coagulation probe or channel formed within a traditional electrosurgical tool such as a spatula, spoon, hook or ball. The invention, however, may be used with any electrosurgical device and is not limited to the examples provided herein.

A preferred embodiment further may have a retractable cover, shutter, or door for protecting the argon plasma coagulation probe or channel during monopolar electrosurgery. To perform argon plasma coagulation, the shutter, door, or cover is opened or drawn back for expose the distal end of the argon plasma coagulation probe or channel.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRITION OF THE DRAWINGS

For a more complete understanding of the present invention and the advantages thereof, reference is now made to the following description and the accompanying drawings, in which:

FIG. 1 illustrates a cross-sectional view of a preferred embodiment of the invention.

DETAILED DESCRIPTION OF THE PREFERRED EMBODIMENTS

Referring to FIG. 1, a preferred embodiment of the combination argon plasma coagulation and monopolar electrosurgy device will be described. It will be apparent to those of skill in the art that the device could be any of various sizes depending on whether it is desired to sue the device in open surgery or in minimally invasive surgery such as laparoscopy or endoscopy.

A preferred embodiment has a spatula tip 110 for performing traditional monopolar eletrosurgery. The spatula tip 110 has a neck 112 and a plurality of members 114 extending from the neck and forming the spatula. In a preferred embodiment, the spatula tip 110 has three members 114, but those skilled in the art will understand that the spatula could be formed using two members 114 or more than three members 114. The members 114 are biased to a position in which an opening 180 exists between the members 114 when the members 114 are not compressed together. The spatula tip 110 may be formed from various conductive materials, including but not limited to steel, tungsten, titanium, zirconium, molybdenum and the like. The spatula tip 110 likewise may be formed from one material, such as steel, and be coated with another, such as tungsten. The spatula tip 110 likewise could be formed from a combination of conductive and non-conductive materials provided that the combination permits conduction of energy to the portion of the spatula that is to be used for monopolar electrosurgery. The spatula tip 110 is connected to a source of RF energy for performing monopolar electrosurgery.

The spatula tip 110 is connected to a shaft or colliery 130. Such connection may be made through a variety of means, such as having a threaded portion at the distal end of the shaft 130 that is engaged by a threaded portion on the neck 112 of the spatula tip 110. In FIG. 2, the spatula tip 110 is shown as being inside the shaft 130, but it should be understood that such structure could be inverted such that the spatula tip 110 is connected to the outside of the shaft 130. The colliery 130 either has an outer surface 132 and is hollow or has a channel therein. A portion of the outer surface in a preferred embodiment has a threaded portion 134. In FIG. 2, the threaded portion 134 of the shaft or colliery 130 is locating near the midpoint of the colliery, but the threaded portion could be placed anywhere on the outer surface 132 or even on the inside of the colliery if it is hollow.

A hollow collet 120 is placed on the shaft 130. The collet 120 extends at least from the neck 112 of the spatula tip 110 to the threaded portion of the shaft 130. The collet 120 has a threaded portion 122 for engaging with the threaded portion of the shaft 130. The collet 120 is a length such that when the threaded portion 122 of the collet 120 is fully engaged with the threaded portion 134 of the shaft 130 the members 114 of the spatula tip 110 are in position such that an opening exists between the members 114 and when threaded portions 122 and 134 are at least partially disengaged the members 114 are compressed together to thereby substantially close any opening between the members 114.

The spatula tip 110 is connected to a generator or source of RF energy 160 through any of a variety of means, such as a wire (not shown) within the shaft 130 and collet 120. The wire may be connected to the spatula tip 110 at any point on the such that the RF energy is conducted to the working portion of the spatula. In a preferred embodiment, the wire is connected to the neck 112 of the spatula tip 110.

In a preferred embodiment, an argon plasma coagulation (APC) probe 140 runs inside the shaft 130, the collet 120, and the spatula tip 110 such that a distal end of the tube is near the opening 180 that exists in the spatula tip 114 when the members 114 are not compressed together. In a preferred embodiment the distal end of the tube is within approximately 1 centimeter of the opening 180, and more preferably less than 5 millimeters from the opening 180.

In one embodiment, the APC probe 140 has a structure such as is disclosed in U.S. Pat. No. 5,207,675. Such a probe has a flexible elongated tube 140 and a wire 144 inside of it. In FIG. 2, the distal end of the wire 144 is near an opening at the distal end of the flexible tube 142. It will be understood to those of skill in the art that depending on the particular embodiment, the structure of the probe 140 could vary, such as by having an opening in the side of the tube 140 rather than at the end of the tube 140. APC probes having such side openings are known, such as in U.S. Pat. No. 6,197,026. Further, the opening in the tube could have various structures, including but not limited to, being round or being a slit.

The proximal end of the APC probe is connected to sources of RF energy and argon gas through an adapter 150. In FIG. 2, the adapter 150 is shown to be connected to generator 160 but it should be understood that the preferred embodiment could be used with any of various known or future developed means for connected such an APC probe to sources of RF energy and argon gas. While the preferred embodiment refers to argon and APC, the present invention should be understood to encompass the use of other inert gases besides argon.

While the preferred embodiment shown in FIG. 1 uses an APC probe, other embodiments will be apparent to those of skill in the art. For example, rather than being hollow, the shaft could have an insulated channel therein and an APC wire running along the length of the channel. The argon gas would flow down the channel around the wire to an opening in the spatula tip. In such an embodiment, the spatula tip likely would also have an insulated channel therein through which the APC wire would run.

Other embodiments also are possible. For example, the spatula tip 110 could be formed integral with the shaft 130. The preferred embodiment, however, includes the separate spatula tip 110 to provide a device on which the spatula tip could be replaced with other attachments such as a ball, a hook or other tool useful in monopolar electrosurgery. Such other attachments could be formed in a manner similar to the spatula tip 110 to open and close an APC opening with rotational movement of the collet 120 relative to the shaft 130. Furthermore, other structures besides the shaft/collet structure of the preferred embodiment could be used for opening and closing the shutter, cover or door. Even further, still further embodiments may be formed in which the members of the spatula tip 110 or other surgical tool are biased inward and are pressed outward to create an APC opening in the tool.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A combination surgical device comprising:
    a shaft;
    an electrosurgical tool attached to said shaft, said electrosurgical tool comprising:
        a neck; and
        a plurality of members connected to said neck, said members being movable between first and second positions, wherein an opening exists in said electrosurgical tool when said members are in said first position and such opening is substantially closed when said members are in said second position;
    means connected to said electrosurgical tool for providing RF energy to said electrosurgical tool;
    a collet connected to said shaft, said collet being movable relative to said shaft; wherein movement of said collet relative to said shaft causes said members to move between said first position and said second position; and means for providing an inert ionizable gas and RF energy through said shaft and said electrosurgical tool to said opening in said electrosurgical tool.

2. A combination surgical device according to claim 1 wherein said inert ionizable gas comprises argon.

3. A combination surgical device according to claim 1 wherein said plurality of members form a spatula.

4. A combination surgical device according to claim 3 wherein said spatula is formed by three of said plurality of members.

5. A combination surgical device according to claim 1 wherein said plurality of members comprises two members.

6. A combination surgical device according to claim 1 wherein said plurality of members are biased toward said second position.

7. A combination surgical device according to claim 1 further comprising means for biasing said plurality of members toward one of said first and second positions.

* * * * *